US00PP14759P3

(12) United States Plant Patent
May

(10) Patent No.: US PP14,759 P3
(45) Date of Patent: May 4, 2004

(54) CHRYSANTHEMUM PLANT NAMED 'JMAY02'

(50) Latin Name: *Chrysanthemum morifolium*
Varietal Denomination: JMay02

(76) Inventor: James D. May, 114 Fel Mar Dr., San Luis Obispo, CA (US) 93405

( * ) Notice: Subject to any disclaimer, the term of this patent is extended or adjusted under 35 U.S.C. 154(b) by 4 days.

(21) Appl. No.: 10/207,647

(22) Filed: Jul. 26, 2002

(65) Prior Publication Data

US 2004/0019946 P1 Jan. 29, 2004

(51) Int. Cl.[7] ..... A01H 5/00
(52) U.S. Cl. ..... Plt./286

(58) Field of Search ..... Plt./286

(56) References Cited

U.S. PATENT DOCUMENTS

PP8,464 P 11/1993 VandenBerg ..... Plt./286

*Primary Examiner*—Anne Marie Grunberg
*Assistant Examiner*—June Hwu
(74) *Attorney, Agent, or Firm*—Knobbe, Martens, Olson & Bear, LLP

(57) ABSTRACT

A new and distinct Chrysanthemum plant cultivar is disclosed, characterized by having a large (10–12 cm) daisy flower form with golden yellow ray florets that have a distinctive red streaking. The floral longevity is very good, and the overall plant vigor is excellent.

1 Drawing Sheet

Latin name of the genus and species: The present invention relates to a new and distinct cultivar of Chrysanthemum plant, botanically known as *Chrysanthemum morifolium.*

Variety denomination: The new and distinct Chrysanthemum plant is hereinafter referred to by the cultivar name 'JMay02'.

BACKGROUND OF THE INVENTION

The new cultivar is a discovered natural mutation. The new cultivar was discovered in a cultivated area and selected by the inventor in a controlled environment in October 2001.

Asexual reproduction of the new cultivar by cuttings was performed in San Luis Obispo, Calif. and has shown that the unique features of this cultivar are stable and reproduced true to type on successive generations.

SUMMARY OF THE INVENTION

The cultivar 'JMay02' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'JMay02'. These characteristics in combination distinguish 'JMay02' as a new and distinct Chrysanthemum cultivar:

1. The flowers have Golden yellow petals with red brushstroke stripes.
2. The flowers are large (10–12 cm) and of daisy flower form.
3. The plant has a strong, spreading growth habit with slightly sparse foliage.
4. The branching habit is four to six breaks per stem on a single pinch.

5. Floral longevity is very good. Flower color intensity fades with time.
6. Plants have excellent vigor and strong stems.
7. The brushstroke characteristic on ray floret petals is distinctive and very unique.

Plants of the new cultivar are similar to plants of the parent variety 'Pelee' (U.S. Plant Pat. No. 8,464) in most horticultural characteristics, such as growth habit, longevity, and plant vigor. However, in contrast to 'Pelee', plants of the new variety have a distinct flower petal color having red streaking on a yellow background.

Plants of the new cultivar are similar to plants of a comparable variety 'Fire Island'. In constrast to 'Fire Island', 'JMay02' flower petal color is yellow with red brushstrokes or streaking. Additionally, 'JMay02' petals have an acute rather than obtuse tip, and the flowers also tend to reflex less than in the comparable variety 'Fire Island'. The flower color of 'JMay02' fades more quickly than in 'Fire Island'. The disc corolla is also more rounded than in 'Fire Island'. Further, the growth habit of 'JMay02' is slightly less vigorous, more spreading and less upright than in 'Fire Island'. The foliage color is lighter, more sparse, and more subdued than in 'Fire Island'.

BRIEF DESCRIPTION OF THE PHOTOGRAPH

The accompanying colored photograph illustrates the overall appearance of the new Chrysanthemum, showing the colors as true as it is reasonably possible to obtain in colored reproductions of this type. Colors in the photographs may differ slightly from the color values cited in the detailed botanical description which accurately describe the colors of the new Chrysanthemum; and shows a top view of a plant of 'JMay02' in full bloom, growing in a 6.5 inch container. Five cuttings were used in the container.

DETAILED BOTANICAL DESCRIPTION

In the following description, color references are made to The Royal Horticultural Society Colour Chart except where general terms of ordinary dictionary significance are used. The following observations and measurements describe plants grown in San Luis Obispo, Calif., during Spring 2002. The plants were grown in a greenhouse with a growing temperature ranging from 65° to 70° F. at night to 70° to 75° F. during the day. The observed plants were approximately 72 days old as measured from the date of rooting of the cutting. The observed plants were first grown for 16 days with "long day" light conditions, then switched to "short day" conditions for the last 56 days. Measurements and numerical values represent averages of typical flowering types.

Botanical classification: *Chrysanthemum morifolium* cultivar 'JMay02'.
Commercial classification: Florist Chrysanthemum.
Parentage: 'JMay02' is a natural mutation of the parent variety 'Pelee' (U.S. Plant Pat. No. 8,464).

PROPAGATION

Time to initiate roots:
*Summer.*—Approximately 3–5 days at 72° F.
*Winter.*—Approximately 4–6 days at 72° F.
Time to develop roots:
*Summer.*—Approximately 8–12 days at 72° F.
*Winter.*—Approximately 10–14 days at 72° F.

PLANT

Plant type: Herbaceous perennial.
Growth habit: Semi-spreading.
Height: Approximately 25–35 cm as a disbud pot mum with 0–7 long days after pinch.
Spread: Approximately 40–45 cm.
Growth rate: Approximately 3–4 cm per week after pinch.
Disease resistance: Very good to excellent resistance to most common chrysanthemum diseases.
Longevity: Flowers last for two to four weeks in a presentable state.
Branches:
*Branching characteristics.*—Freely branching.
*Length of lateral branches.*—Approximately 20–25 cm.
*Diameter of lateral branches.*—Approximately 4–6 mm.
*Number of leaves per lateral branch.*—Approximately 13–15.
Stems:
*Stem internode length.*—Approximately 2–8 cm.
*Stem color.*—About 138C RHS.
*Stem and stem base strength.*—Very strong.
*Stem texture.*—Pubescent.
*Stem growth habit.*—Ascending.
Roots:
*Rooting habit.*—Vigorous and well-branched.
*Root texture.*—Fibrous.

FOLIAGE

Leaf:
*Arrangement.*—Alternate.
*Leaf type.*—Simple.
*Leaf width.*—Juvenile Leaf — width: Approximately 10–15 mm. Mature Leaf — width: Approximately 50–70 mm.
*Leaf length:* (*base to apex*).—Juvenile Leaf — length: Approximately 25–30 mm. Mature Leaf — length: Approximately 90–110 mm.
*Leaf shape.*—Lanceolate to ovate (moderately to deeply lobed and slightly serrate).
*Shape of blade.*—Simple.
*Apex.*—Acute (slightly serrate).
*Base.*—Attenuate.
*Attachment.*—Attenuate to stem.
*Leaf aspect.*—Juvenile leaves slightly cupped, changing at times to slightly recurved in mature foliage.
*Margin.*—Moderately to deeply lobed and slightly serrate.
*Texture of top surface.*—Canescent.
*Texture of bottom surface.*—Pubescent.
*Color.*—Young foliage upper side: Approximately 141A RHS. Young foliage under side: Approximately 138B RHS. Mature foliage upper side: Approximately 139A RHS. Mature foliage under side: Approximately 137C RHS. Venation upper side: Approximately 138B RHS. Venation under side: Approximately 139C RHS. Venation Pattern: Palmate.
Stipule:
*Stipule number.*—Two per leaf.
*Stipule size.*—About 8 mm by 10 mm.
*Stipule shape.*—Deltoid.
*Foliage durability.*—Foliage is very durable throughout the length of the stem.
*Stipule color* (*upper side*).—Approximately 136A RHS.
*Stipule color* (*under side*).—Approximately 137A RHS.
Petiole:
*No real petiole.*—Leaf is attenuate to stem.

INFLORESCENCE

Inflorescence characteristics:
*Flowering habit.*—Requires a minimum of 12 hours darkness per day in order to initiate floral induction and bud development.
*Flowering induction.*—Twelve hours of darkness per day for 52–58 days required to develop blooms.
*Inflorescence form.*—Flat capitulum type daisy.
*Natural flowering season.*—Fall.
*Number of inflorescences per lateral branch.*—Approximately one, after disbudding the stem. Six to eight, without disbudding.
*Inflorescence diameter.*—Approximately 10–12 cm.
*Inflorescence depth.*—Approximately 2–3 cm.
*Inflorescence longevity on plant.*—Approximately 21–28 days.
*Persistence.*—Persistent.
*Disc diameter.*—Approximately 2 cm.
Ray florets:
*Arrangement.*—Ray florets arranged in multiple layers around disc florets.
*Texture.*—Smooth to satiny.
*Average number per flower.*—Approximately 30–35.
*Shape.*—Elliptic.
*Apex.*—Acute.
*Aspect.*—Approximately 15–90 degrees from vertical.
*Margin.*—Entire.
*Length.*—Approximately 5 cm.
*Width.*—Approximately 2 cm.

*Color.*—Upper surface at first opening: Near 9A and 34A RHS. Upper surface at maturity: Near 9B and 172A RHS. Under surface at first opening: Near 12B and 180A with 5B overtones RHS. Under surface at maturity: Near 12B and 180B with 5C overtones RHS.

*Color changes as the ray flower ages.*—Red streaking is in sharp contrast to yellow background as the flower first opens. Streaking fades somewhat as flower matures, but is still distinct as multiple brush-strokes or streaking over yellow background.

*Ray floret pistils.*—Number of pistils per flower: One. Stigma shape: 2 Branched. Stigma color: Near 7A. Style color: Near 1A. Style length: Approximately 4–5 mm.

Disc florets:

*Appearance.*—Glossy.

*Texture.*—Satiny smooth.

*Average number per flower.*—Numerous, approximately 200 to 400.

*Shape.*—Tubular.

*Apex.*—5 acute incurved tips.

*Average length.*—Approximately 6–8 mm.

*Average width.*—Approximately 1–2 mm.

*Color.*—At first opening: Near 151A. At maturity: Near 7A.

*Changes in the disc floret upon aging.*—Disc florets mature exposing stigmas from outer edge of disc towards the center.

*Disc flower pistils.*—Number of pistils per flower: One. Stigma shape: 2 Branched. Stigma color: Near 7A. Style color: Near 1A. Style length: Approximately 4–5 mm.

*Disc flower stamens.*—Number of stamens per flower: 5. Anther shape: Syngenesious. Anther color: Near 7A. Pollen color: Near 7A. Pollen Quantity: Low — very little present.

Peduncle:

*Length.*—At terminal end (shortest): Approximately 1 cm. At lateral end (longest): Approximately 4 cm.

*Diameter.*—Approximately 4–5 mm.

*Angle to stem.*—10–30 degrees.

*Strength.*—Strong.

*Color.*—Near 138D RHS.

*Habit.*—Erect.

*Surface.*—Pubescent.

Inflorescence bud:

*Length.*—Approximately 8–10 mm.

*Diameter.*—Approximately 12–14 mm.

*Form.*—Globular.

*Color.*—Near 141A RHS.

*Rate of flower opening.*—Approximately 14–21 days.

Involucral bracts (phyllaries):

*Appearance.*—Matte.

*Arrangement.*—Whorled.

*Texture.*—Pubescent.

*Number.*—Approximately 30–50.

*Shape.*—Ovate.

*Margin.*—Entire.

*Apex.*—Acute.

*Length.*—Approximately 8–14 mm.

*Width.*—Approximately 3–5 mm.

*Color.*—Upper side: Near 134A RHS. Under side: Near 141A RHS.

OTHER CHARACTERISTICS

Seed production: Commercially, this plant is not used or observed in a stage wherein seeds would be produced. Therefore, seed production has not been observed.

What is claimed is:

1. A new and distinct cultivar of Chrysanthemum plant named 'JMay02' as herein illustrated and described.

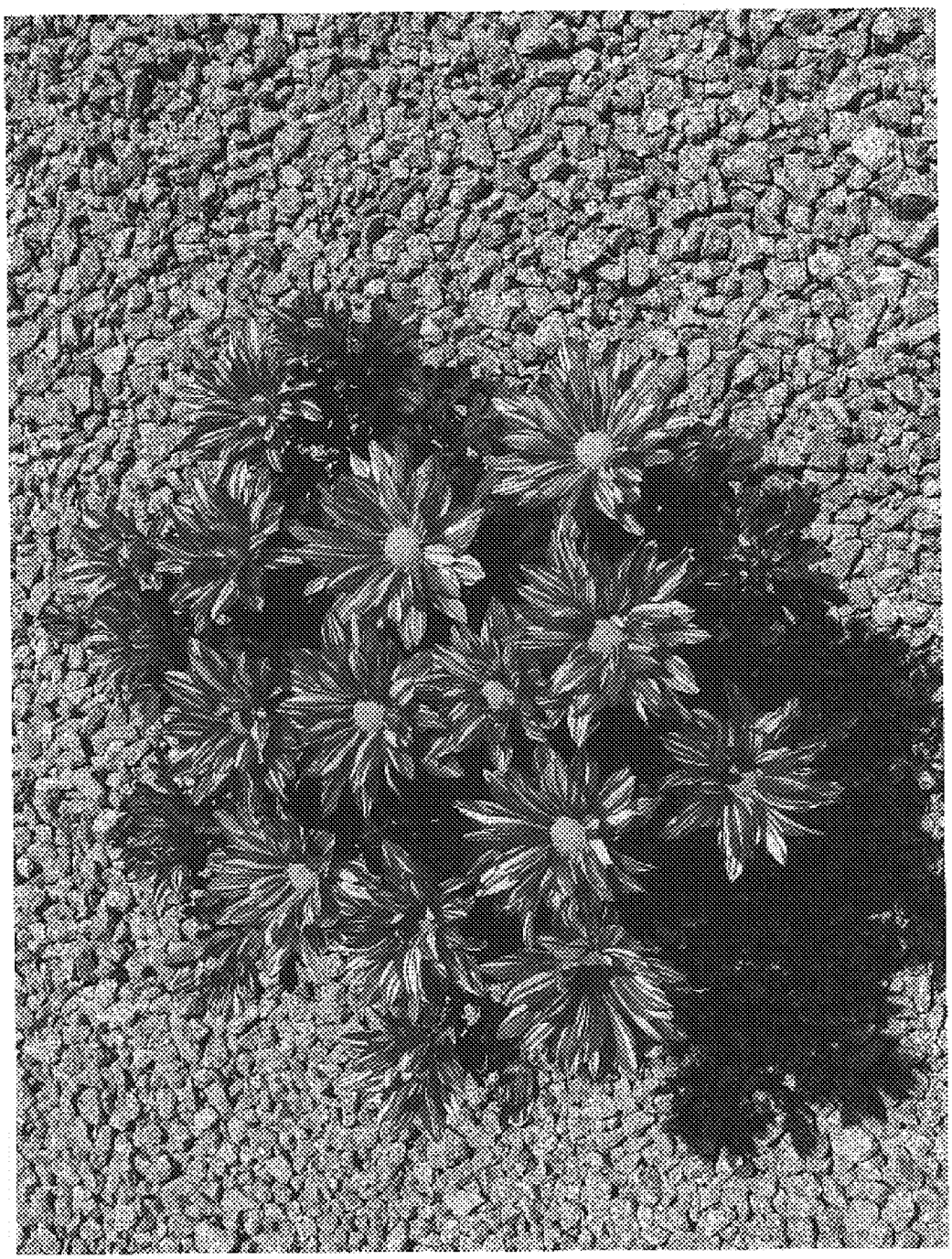

* * * * *